United States Patent
Norris et al.

(10) Patent No.: US 10,117,765 B2
(45) Date of Patent: *Nov. 6, 2018

(54) APPOSITION FIBER FOR USE IN ENDOLUMINAL DEPLOYMENT OF EXPANDABLE IMPLANTS

(75) Inventors: Patrick M. Norris, Bellemont, AZ (US); Joseph M. Viskocil, Flagstaff, AZ (US)

(73) Assignee: W.L. Gore Associates, Inc, Newark, DE (US)

( * ) Notice: Subject to any disclaimer, the term of this patent is extended or adjusted under 35 U.S.C. 154(b) by 584 days.

This patent is subject to a terminal disclaimer.

(21) Appl. No.: 13/495,776

(22) Filed: Jun. 13, 2012

(65) Prior Publication Data

US 2013/0158647 A1  Jun. 20, 2013

Related U.S. Application Data

(60) Provisional application No. 61/496,966, filed on Jun. 14, 2011.

(51) Int. Cl.
*A61F 2/97* (2013.01)
*A61F 2/95* (2013.01)

(52) U.S. Cl.
CPC ......... *A61F 2/97* (2013.01); *A61F 2002/9511* (2013.01)

(58) Field of Classification Search
CPC .................................. A61F 2/95–2/97; A61F 2002/9505–2002/9665
USPC ................................ 606/108; 623/1.11–1.23
See application file for complete search history.

(56) References Cited

U.S. PATENT DOCUMENTS

| | | | |
|---|---|---|---|
| 1,851,314 A | 3/1932 | Knoche | |
| 3,625,451 A | 12/1971 | Anderson | |
| 3,915,167 A | 10/1975 | Waterman | |
| 4,655,246 A | 4/1987 | Philipot et al. | |

(Continued)

FOREIGN PATENT DOCUMENTS

| | | |
|---|---|---|
| CN | 101554343 | 10/2009 |
| CN | 101780306 A | 7/2010 |

(Continued)

OTHER PUBLICATIONS

Ueda et al, Incomplete Endograft Apposition to the Aortic Arch: Bird-Beak Configuration Increases Risk of Endoleak Formation after Thoracic Endovascular Aortic Repair, Radiology: vol. 255 No. 2; May 2010, pp. 645-652.

(Continued)

*Primary Examiner* — Darwin Erezo
*Assistant Examiner* — Jonathan Hollm

(57) ABSTRACT

The present disclosure describes treatment of the vasculature of a patient with an expandable implant. The implant is constrained to a reduced delivery diameter for delivery within the vasculature by at least one sleeve. The implant can be constrained to other diameters, such as an intermediate diameter. The sleeves can be expanded, allowing for expansion of the diameter of the expandable implant, by disengaging a coupling member from the sleeve or sleeves from outside of the body of the patient. The expandable implant can comprise an apposition line or lines which facilitate bending of the expandable implant to improve conformation of the expandable implant to the vasculature of the patient.

20 Claims, 14 Drawing Sheets

(56) References Cited

U.S. PATENT DOCUMENTS

| | | | |
|---|---|---|---|
| 4,858,810 A | 8/1989 | Intlekofer | |
| 5,217,486 A | 6/1993 | Rice et al. | |
| 5,325,746 A | 7/1994 | Anderson | |
| 5,344,427 A | 9/1994 | Cottenceau et al. | |
| 5,527,338 A | 6/1996 | Purdy | |
| 5,554,183 A | 9/1996 | Nazari | |
| 5,562,726 A | 10/1996 | Chuter | |
| 5,693,083 A * | 12/1997 | Baker et al. | 623/1.11 |
| 5,707,376 A | 1/1998 | Kavteladze et al. | |
| 5,709,704 A | 1/1998 | Nott et al. | |
| 5,713,917 A | 2/1998 | Leonhardt et al. | |
| 5,713,948 A | 2/1998 | Uflacker | |
| 5,720,776 A | 2/1998 | Chuter et al. | |
| 5,725,552 A | 3/1998 | Kotula | |
| 5,776,141 A | 7/1998 | Klein et al. | |
| 5,776,186 A | 7/1998 | Uflacker | |
| 5,782,909 A | 7/1998 | Quiachon et al. | |
| 5,843,162 A | 12/1998 | Inoue | |
| 5,873,906 A | 2/1999 | Lau et al. | |
| 5,904,703 A | 5/1999 | Gilson | |
| 5,961,546 A | 10/1999 | Robinson et al. | |
| 6,013,093 A | 1/2000 | Nott et al. | |
| 6,015,431 A | 1/2000 | Thornton et al. | |
| 6,019,785 A | 2/2000 | Strecker | |
| 6,143,021 A | 11/2000 | Staeghle | |
| 6,152,144 A | 11/2000 | Lesh | |
| 6,165,195 A | 12/2000 | Wilson | |
| 6,214,025 B1 | 4/2001 | Thistle et al. | |
| 6,224,627 B1 | 5/2001 | Armstrong et al. | |
| 6,231,561 B1 | 5/2001 | Frazier et al. | |
| 6,231,581 B1 | 5/2001 | Shank et al. | |
| 6,231,589 B1 | 5/2001 | Wessman et al. | |
| 6,264,671 B1 | 7/2001 | Stack | |
| 6,273,900 B1 | 8/2001 | Nott et al. | |
| 6,322,585 B1 | 11/2001 | Khosravi et al. | |
| 6,328,727 B1 | 12/2001 | Frazier et al. | |
| 6,346,117 B1 | 2/2002 | Greenhalgh | |
| 6,352,561 B1 | 3/2002 | Leopold et al. | |
| 6,451,051 B2 | 9/2002 | Drasler et al. | |
| 6,485,513 B1 | 11/2002 | fan | |
| 6,491,704 B2 | 12/2002 | Gifford, III et al. | |
| 6,524,335 B1 | 2/2003 | Hartley et al. | |
| 6,527,779 B1 | 3/2003 | Rourke | |
| 6,551,303 B1 | 4/2003 | Van Tessel et al. | |
| 6,551,350 B1 * | 4/2003 | Thornton et al. | 623/1.13 |
| 6,572,643 B1 | 6/2003 | Gharibadeh | |
| 6,572,646 B1 | 6/2003 | Boylan et al. | |
| 6,689,150 B1 | 2/2004 | Van Tassel | |
| 6,705,563 B2 | 3/2004 | Luo et al. | |
| 6,712,836 B1 | 3/2004 | Berg et al. | |
| 6,712,842 B1 | 3/2004 | Gifford, III et al. | |
| 6,730,108 B2 | 5/2004 | Van Tassel | |
| 6,743,210 B2 | 6/2004 | Hart et al. | |
| 6,746,472 B2 | 6/2004 | Frazier et al. | |
| 6,755,854 B2 | 6/2004 | Gillick et al. | |
| 6,827,731 B2 | 12/2004 | Armstrong et al. | |
| 6,866,669 B2 | 3/2005 | Buzzard et al. | |
| 6,884,259 B2 | 4/2005 | Tran et al. | |
| 6,926,732 B2 | 8/2005 | Derus et al. | |
| 6,939,352 B2 | 9/2005 | Buzzard et al. | |
| 6,945,990 B2 * | 9/2005 | Greenan | 623/1.12 |
| 6,949,113 B2 | 9/2005 | Van Tassel | |
| 6,974,471 B2 * | 12/2005 | Van Schie et al. | 623/1.12 |
| 6,994,092 B2 | 2/2006 | Van Der Burg et al. | |
| 7,033,368 B2 | 4/2006 | Rourke | |
| 7,044,134 B2 | 5/2006 | Khairkhahan | |
| 7,049,380 B1 | 5/2006 | Chang et al. | |
| 7,052,511 B2 | 5/2006 | Weldon et al. | |
| 7,066,951 B2 | 6/2006 | Chovotov | |
| 7,122,050 B2 | 10/2006 | Randall et al. | |
| 7,128,073 B1 | 10/2006 | Van Der Burg et al. | |
| 7,147,657 B2 | 12/2006 | Chiang et al. | |
| 7,169,160 B1 | 1/2007 | Middleman et al. | |
| 7,198,636 B2 | 4/2007 | Cully et al. | |
| 7,208,003 B2 | 4/2007 | Davis et al. | |
| 7,252,680 B2 | 8/2007 | Freitag | |
| 7,331,992 B2 | 2/2008 | Randall et al. | |
| 7,396,359 B1 | 7/2008 | DeRowe | |
| 7,462,675 B2 | 12/2008 | Chang et al. | |
| 7,566,336 B2 | 7/2009 | Corcoran et al. | |
| 7,572,289 B2 | 8/2009 | Sisken et al. | |
| 7,601,159 B2 | 10/2009 | Ewers et al. | |
| 7,611,528 B2 | 11/2009 | Goodson et al. | |
| 7,655,034 B2 | 2/2010 | Mitchell et al. | |
| 7,771,455 B2 | 8/2010 | Ken | |
| 7,815,591 B2 | 10/2010 | Levine et al. | |
| 7,846,179 B2 | 12/2010 | Belef et al. | |
| 7,887,580 B2 | 2/2011 | Randall et al. | |
| 7,976,575 B2 | 7/2011 | Hartley | |
| 7,998,189 B2 | 8/2011 | Kolbel et al. | |
| 8,029,559 B2 | 10/2011 | Sisken et al. | |
| 8,048,440 B2 | 11/2011 | Chang | |
| 8,062,349 B2 | 11/2011 | Moore et al. | |
| 8,080,032 B2 | 12/2011 | van der Burg | |
| 8,231,650 B2 | 7/2012 | Cully | |
| 8,241,350 B2 | 8/2012 | Randall et al. | |
| 8,273,105 B2 | 9/2012 | Cohen et al. | |
| 8,287,583 B2 | 10/2012 | LaDuca et al. | |
| 8,424,166 B2 | 4/2013 | Dorneman et al. | |
| 8,449,595 B2 | 5/2013 | Ouellette et al. | |
| 8,469,990 B2 | 6/2013 | McGuckin | |
| 8,523,897 B2 | 9/2013 | van der Burg | |
| 8,529,597 B2 | 9/2013 | Linder | |
| 8,685,055 B2 | 4/2014 | Van Tassel | |
| 8,834,519 B2 | 9/2014 | van der Burg | |
| 8,870,947 B2 | 10/2014 | Shaw | |
| 9,095,466 B2 | 8/2015 | Norris | |
| 9,254,204 B2 | 2/2016 | Roeder | |
| 2001/0037142 A1 | 11/2001 | Stelter et al. | |
| 2002/0007208 A1 | 1/2002 | Strecker | |
| 2002/0029077 A1 | 3/2002 | Leopold et al. | |
| 2002/0099431 A1 * | 7/2002 | Armstrong et al. | 623/1.11 |
| 2002/0151953 A1 | 10/2002 | Chobotov et al. | |
| 2003/0098383 A1 | 5/2003 | Luo et al. | |
| 2003/0149467 A1 | 8/2003 | Linder et al. | |
| 2003/0181942 A1 | 9/2003 | Sutton | |
| 2004/0034366 A1 | 2/2004 | Van der Burg et al. | |
| 2004/0054396 A1 | 3/2004 | Hartley et al. | |
| 2004/0073289 A1 | 4/2004 | Hartley | |
| 2004/0122503 A1 | 6/2004 | Campbell et al. | |
| 2004/0138734 A1 * | 7/2004 | Chobotov et al. | 623/1.11 |
| 2004/0143315 A1 | 7/2004 | Bruun et al. | |
| 2005/0049667 A1 | 3/2005 | Arbefeuille et al. | |
| 2005/0070820 A1 | 3/2005 | Boutillette | |
| 2005/0080476 A1 | 4/2005 | Gunderson et al. | |
| 2005/0085890 A1 * | 4/2005 | Rasmussen | A61F 2/95 623/1.11 |
| 2005/0125031 A1 | 6/2005 | Pipenhagen et al. | |
| 2005/0240257 A1 * | 10/2005 | Ishimaru et al. | 623/1.15 |
| 2006/0004433 A1 | 1/2006 | Greenberg et al. | |
| 2006/0015171 A1 | 1/2006 | Armstrong | |
| 2006/0058833 A1 | 3/2006 | Vancamp | |
| 2006/0155366 A1 | 7/2006 | LaDuca et al. | |
| 2006/0254569 A1 | 11/2006 | Chipman | |
| 2006/0264980 A1 | 11/2006 | Khairkhahan | |
| 2007/0066993 A1 | 3/2007 | Kreidler | |
| 2007/0088424 A1 * | 4/2007 | Greenberg | A61F 2/954 623/1.12 |
| 2007/0100427 A1 | 5/2007 | Perouse | |
| 2007/0162048 A1 | 7/2007 | Quinn et al. | |
| 2007/0167955 A1 | 7/2007 | Arnault de la Menardiere et al. | |
| 2007/0198077 A1 | 8/2007 | Cully et al. | |
| 2007/0198078 A1 | 8/2007 | Berra et al. | |
| 2007/0219467 A1 | 9/2007 | Clark | |
| 2007/0248640 A1 | 10/2007 | Karabey et al. | |
| 2007/0249980 A1 | 10/2007 | Carrez et al. | |
| 2007/0255390 A1 | 11/2007 | Ducke et al. | |
| 2007/0270891 A1 | 11/2007 | McGuckin | |
| 2008/0027529 A1 | 1/2008 | Hartley et al. | |
| 2008/0178434 A1 | 1/2008 | Bulanda | |
| 2008/0039925 A1 * | 2/2008 | Ishimaru et al. | 623/1.12 |
| 2008/0114440 A1 * | 5/2008 | Hlavka et al. | 623/1.12 |
| 2008/0147111 A1 | 6/2008 | Johnson | |
| 2008/0208329 A1 | 8/2008 | Bishop | |

(56) References Cited

U.S. PATENT DOCUMENTS

| | | |
|---|---|---|
| 2008/0269785 A1 | 10/2008 | Lampropoulos |
| 2009/0048656 A1* | 2/2009 | Wen .......................... 623/1.12 |
| 2009/0054723 A1 | 2/2009 | Khairkhahan et al. |
| 2009/0062838 A1 | 3/2009 | Brumleve et al. |
| 2009/0082844 A1 | 3/2009 | Zacharias et al. |
| 2009/0099596 A1 | 4/2009 | McGuckin, Jr. |
| 2009/0099640 A1 | 4/2009 | Weng |
| 2009/0112249 A1 | 4/2009 | Miles |
| 2009/0171386 A1 | 7/2009 | Amplatz |
| 2009/0216308 A1* | 8/2009 | Hartley ........................ 623/1.11 |
| 2009/0259291 A1* | 10/2009 | Kolbel et al. ................. 623/1.13 |
| 2010/0016943 A1 | 1/2010 | Chobotov |
| 2010/0023048 A1 | 1/2010 | Mach |
| 2010/0057195 A1 | 3/2010 | Roeder et al. |
| 2010/0094394 A1 | 4/2010 | Beach et al. |
| 2010/0094401 A1 | 4/2010 | Kolbel |
| 2010/0114290 A1 | 5/2010 | Rasmussen |
| 2010/0211052 A1 | 8/2010 | Brown et al. |
| 2010/0280591 A1 | 11/2010 | Shin |
| 2011/0040366 A1 | 2/2011 | Goetz et al. |
| 2011/0054519 A1 | 3/2011 | Neuss |
| 2011/0066221 A1 | 3/2011 | White |
| 2011/0125252 A1* | 5/2011 | Goddard .................. A61F 2/95 623/1.23 |
| 2011/0130821 A1 | 6/2011 | Styrc |
| 2011/0288624 A1* | 11/2011 | Roeder ..................... A61F 2/07 623/1.11 |
| 2011/0313503 A1 | 12/2011 | Berra et al. |
| 2012/0022630 A1 | 1/2012 | Wubbeling |
| 2012/0022638 A1 | 1/2012 | Leewood et al. |
| 2012/0046652 A1 | 2/2012 | Sokel |
| 2012/0130473 A1 | 5/2012 | Norris et al. |
| 2012/0130474 A1 | 5/2012 | Buckley |
| 2012/0130475 A1 | 5/2012 | Shaw |
| 2012/0143305 A1 | 6/2012 | Berra et al. |
| 2012/0172965 A1 | 7/2012 | Kratzberg et al. |
| 2012/0172968 A1 | 7/2012 | Chuter et al. |
| 2012/0283773 A1 | 11/2012 | Van Tassel |
| 2012/0296360 A1 | 11/2012 | Norris et al. |
| 2012/0323270 A1 | 12/2012 | Lee |
| 2013/0023981 A1 | 1/2013 | Dierking et al. |
| 2013/0046371 A1 | 2/2013 | Greenberg et al. |
| 2013/0073029 A1 | 3/2013 | Shaw |
| 2013/0123896 A1 | 5/2013 | Bloss et al. |
| 2013/0138138 A1 | 5/2013 | Clark |
| 2013/0158647 A1 | 6/2013 | Norris et al. |
| 2013/0178889 A1 | 7/2013 | Miles |
| 2013/0245666 A1 | 9/2013 | Larsen et al. |
| 2013/0245742 A1 | 9/2013 | Norris |
| 2013/0296912 A1 | 11/2013 | Ottma |
| 2014/0012303 A1 | 1/2014 | Heipl |
| 2014/0046360 A1 | 2/2014 | van der Burg |
| 2014/0296908 A1 | 10/2014 | Ottma |
| 2014/0296909 A1 | 10/2014 | Heipl |
| 2014/0379019 A1 | 12/2014 | Larsen |
| 2015/0005809 A1 | 1/2015 | Ayres et al. |
| 2015/0005810 A1 | 1/2015 | Center |
| 2015/0051695 A1 | 2/2015 | Shaw |
| 2015/0305749 A1 | 10/2015 | Alferness |
| 2016/0331382 A1 | 11/2016 | Center |
| 2017/0181751 A1 | 6/2017 | Larsen |

FOREIGN PATENT DOCUMENTS

| | | |
|---|---|---|
| CN | 103347467 A | 10/2013 |
| EP | 0664107 A1 | 7/1995 |
| EP | 0679372 | 11/1995 |
| EP | 2481381 | 8/2012 |
| FR | 2896405 A1 | 7/2007 |
| GB | 2344054 A | 5/2000 |
| JP | 1996126704 | 5/1996 |
| JP | 2001506902 A | 7/1998 |
| JP | 2002503114 A | 1/2002 |
| JP | 2002518086 A | 6/2002 |
| JP | 2004167239 A | 6/2004 |
| JP | 2004188219 A | 7/2004 |
| JP | 2007518465 A | 7/2007 |
| JP | 2011511693 A | 4/2011 |
| JP | 2014501563 A | 1/2014 |
| JP | 2014501565 A | 1/2014 |
| JP | 2014502180 A | 1/2014 |
| JP | 2014533189 A | 12/2014 |
| WO | WO-199618361 A1 | 6/1996 |
| WO | WO-199748350 A1 | 12/1997 |
| WO | 1998027894 A1 | 7/1998 |
| WO | WO-199965420 A1 | 12/1999 |
| WO | WO-200013613 A1 | 3/2000 |
| WO | WO-200121109 A1 | 3/2001 |
| WO | WO-200228317 A2 | 4/2002 |
| WO | WO-2007092354 A2 | 8/2004 |
| WO | WO-2008063464 A2 | 5/2005 |
| WO | WO-2005072652 | 8/2005 |
| WO | WO-2006007389 A1 | 1/2006 |
| WO | 2008/047092 | 4/2008 |
| WO | WO-2008047092 A1 | 4/2008 |
| WO | 2009/102441 | 8/2009 |
| WO | 2009126227 A2 | 10/2009 |
| WO | WO-2009148594 A1 | 12/2009 |
| WO | 2010001012 A1 | 1/2010 |
| WO | WO-2010001012 A1 | 1/2010 |
| WO | WO-2010090699 A1 | 1/2010 |
| WO | WO-2010024881 | 3/2010 |
| WO | WO-2010041038 A1 | 4/2010 |
| WO | WO-2010044854 A1 | 4/2010 |
| WO | 2010/063795 | 6/2010 |
| WO | WO-2010063795 A1 | 6/2010 |
| WO | WO-2010081041 | 7/2010 |
| WO | 2010/105195 | 9/2010 |
| WO | WO-2011031981 | 3/2011 |
| WO | 2011/062858 | 5/2011 |
| WO | 2012/068257 | 5/2012 |
| WO | WO-2013040431 A1 | 3/2013 |
| WO | WO-2013137977 A1 | 9/2013 |
| WO | WO-2015132668 A1 | 9/2015 |

OTHER PUBLICATIONS

International Search Report and Written Opinion for PCT/US2012/061928 dated Jan. 22, 2013, corresponding to U.S. Appl. No. 13/658,597, 8 pages.
International Search Report and Written Opinion for PCT/US2013/022404 dated May 8, 2013, corresponding to U.S. Appl. No. 13/743,118, 7 pages.
International Search Report and Written Opinion for PCT/US2014/066153 dated Feb. 17, 2015, corresponding to U.S. Appl. No. 14/084,592, 5 pages.
European Search Report from EP17166472.5, dated Nov. 7, 2017, 7 pages.
European Search Report for European Application No. 16155556.0 dated Aug. 1, 2016, 10 pages.
Hsu et al, The Impact of Bird-Beak Configuration on Aortic Remodeling of Distal Arch Pathology After Thoracic Endovascular Aortic Repair with the Zenith Pro-Form TX2 Thoracic Endograft, Journal of Vascular Surgery, 2013, pp. 1-9.
International Preliminary Report on Patentability for PCT/US2012/055537, dated Mar 18, 2014, 10 pages.
International Preliminary Report on Patentability for PCT/US2012055445 dated Mar 18, 2014, 9 pages.
International Search Report & Written Opinion in International Application No. PCT/US/2012/055445, dated Dec. 5, 2012, 15 pages.
International Search Report and Written Opinion for PCT/US2012/055537, dated Dec. 5, 2012, 5 pages.
International Search Report and Written Opinion from PCT/US2016/032487, dated Dec. 14, 2016, 20 pages.

* cited by examiner

APPOSITION FIBER FOR USE IN ENDOLUMINAL DEPLOYMENT OF EXPANDABLE IMPLANTS

CROSS-REFERENCE TO RELATED APPLICATIONS

This application claims priority to U.S. Provisional Application Ser. No. 61/496,966, entitled "APPOSITION FIBER FOR USE IN ENDOLUMINAL DEPLOYMENT OF EXPANDABLE IMPLANTS IN TORTUOUS ANATOMIES" filed Jun. 14, 2011, which is hereby incorporated by reference in its entirety.

BACKGROUND

Field

The present disclosure relates generally to expandable implants and, more specifically, to orienting and positioning endoluminally-delivered expandable implants within the vasculature of a patient.

Discussion of the Related Art

Endoluminal therapies typically involve the insertion of a delivery catheter to transport a prosthetic implant into the vasculature through a small, often percutaneous, access site in a remote vessel. Once access to the vasculature is achieved, the delivery catheter is used to mediate endoluminal delivery and subsequent deployment of the implant via one of several techniques. In this fashion, the implant can be remotely delivered to achieve a therapeutic outcome. In contrast to conventional surgical therapies, endoluminal treatments are distinguished by their "minimally invasive" nature.

Endoluminally-deliverable expandable implants can be comprised of a graft or a stent component with or without a graft covering over the stent interstices. They can be designed to expand when a restraint is removed or to be balloon-expanded from their delivery diameter, through a range of intermediary diameters, up to a maximal, predetermined functional diameter. The endoluminal delivery and deployment of expandable implants pose several unique problems. For example, the expandable implant itself must be constrained in a suitable introductory size (or delivery diameter) to allow insertion into the vasculature and mounted onto a delivery device such as a catheter shaft. In such configurations, the expandable implant can be difficult to navigate through vasculature that has significant bending or curvature.

Therefore, it is desirable to provide systems for endoluminal delivery of expandable implants to vascular treatment sites, particularly along tortuous vasculature, such as along the aortic arch.

BRIEF DESCRIPTION OF THE DRAWINGS

The accompanying drawings are included to provide a further understanding of the disclosure and are incorporated in and constitute a part of this specification, illustrate embodiments of the disclosure and together with the description serve to explain the principles of the disclosure, wherein.

DETAILED DESCRIPTION OF THE ILLUSTRATED EMBODIMENTS

Figure 1:
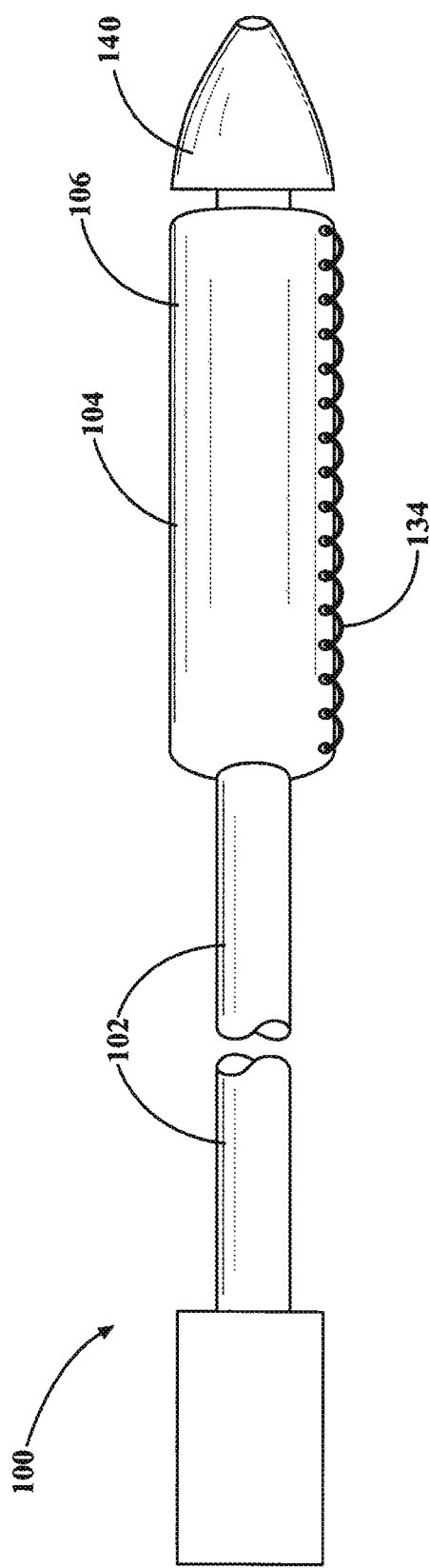
FIG. 1 illustrates a side view of a catheter assembly having an expandable implant in accordance with the present disclosure.

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting. Finally, although the present disclosure can be described in connection with various principles and beliefs, the present disclosure should not be bound by theory.

Throughout this specification and in the claims, the term "distal" refers to a location that is, or a portion of an expandable implant (such as a stent-graft) that when implanted is, further downstream with respect to blood flow than another portion of the implant. Similarly, the term "distally" refers to the direction of blood flow or further downstream in the direction of blood flow.

The term "proximal" refers to a location that is, or a portion of an expandable implant that when implanted is, further upstream with respect to blood flow than another portion of the implant. Similarly, the term "proximally" refers to the direction opposite to the direction of blood flow or upstream from the direction of blood flow.

With further regard to the terms proximal and distal, and because the present disclosure is not limited to peripheral and/or central approaches, this disclosure should not be narrowly construed with respect to these terms. Rather, the implants and methods described herein can be altered and/or adjusted relative to the anatomy of a patient.

Throughout this specification and in the claims, the term "leading" refers to a relative location on a catheter assembly which is closer to the end of an implant that is inserted into and progressed through the vasculature of a patient. The term "trailing" refers to a relative location on a catheter assembly which is closer to the end of an implant that is located outside of the vasculature of a patient.

In various embodiments, a catheter assembly is disclosed which utilizes one or more flexible sleeves that (i) releasably constrain an expandable implant, such as an expandable stent graft, in a dimension suitable for endoluminal delivery of the implant to a treatment site, such as a vascular member in a patient's body; and (ii) further constrain the implant to an outer peripheral dimension that is larger than the dimension suitable for endoluminal delivery but smaller than an unconstrained or fully deployed outer peripheral dimension, thereby facilitating selective axial and/or rotational positioning of the implant at the treatment site prior to full deployment and expansion of the implant.

Various embodiments of the present disclosure comprise a catheter assembly configured to deliver an expandable implant to a treatment area of the vasculature of a patient. In accordance with embodiments of the disclosure, the catheter assembly includes at least one apposition line. The apposition line (or lines) allows for selective bending of the expandable implant within the vasculature.

With initial reference to FIG. 1, a catheter assembly 100 in accordance with the present disclosure comprises an expandable implant 106. Expandable implant 106 can comprise any endoluminally-delivered expandable implant suitable for delivery to the treatment area of a vasculature. Such implants can include, for example, stents, grafts, and stent grafts.

In various embodiments, expandable implant 106 comprises a stent graft. Conventional stent grafts are designed to dilate from their delivery diameter, through a range of intermediary diameters, up to a maximal, pre-determined functional diameter, and generally comprise one or more stent components with one or more graft members displaced over and/or under the stent.

In various embodiments, expandable implant 106 comprises one or more stent components made of nitinol and a graft member made of ePTFE. However, and as discussed below, any suitable combination of stent component(s) and graft member(s) is within the scope of the present disclosure.

Stent components can have various configurations such as, for example, rings, cut tubes, wound wires (or ribbons) or flat patterned sheets rolled into a tubular form.

Stent components can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol and biologically derived materials such as bovine arteries/veins, pericardium and collagen. Stent components can also comprise bioresorbable materials such as poly(amino acids), poly(anhydrides), poly(caprolactones), poly(lactic/glycolic acid) polymers, poly(hydroxybutyrates) and poly(orthoesters). Any expandable stent component configuration which can be delivered by a catheter is in accordance with the present disclosure.

Moreover, potential materials for graft members include, for example, expanded polytetrafluoroethylene (ePTFE), polyester, polyurethane, fluoropolymers, such as perfouorelastomers and the like, polytetrafluoroethylene, silicones, urethanes, ultra high molecular weight polyethylene, aramid fibers, and combinations thereof. Other embodiments for a graft member material can include high strength polymer fibers such as ultra high molecular weight polyethylene fibers (e.g., Spectra®, Dyneema Purity®, etc.) or aramid fibers (e.g., Technora®, etc.). The graft member can include a bioactive agent. In one embodiment, an ePTFE graft includes a carbon component along a blood contacting surface thereof. Any graft member that can be delivered by a catheter is in accordance with the present disclosure.

In various embodiments, a stent component and/or graft member can comprise a therapeutic coating. In these embodiments, the interior or exterior of the stent component and/or graft member can be coated with, for example, a CD34 antigen. Additionally, any number of drugs or therapeutic agents can be used to coat the graft member, including, for example heparin, sirolimus, paclitaxel, everolimus, ABT-578, mycophenolic acid, tacrolimus, estradiol, oxygen free radical scavenger, biolimus A9, anti-CD34 antibodies, PDGF receptor blockers, MMP-1 receptor blockers, VEGF, G-CSF, HMG-CoA reductase inhibitors, stimulators of iNOS and eNOS, ACE inhibitors, ARBs, doxycycline, and thalidomide, among others.

In various embodiments, expandable implant 106 can comprise a radially collapsed configuration suitable for delivery to the treatment area of the vasculature of a patient. Expandable implant 106 can be constrained in a radially collapsed configuration and mounted onto a delivery device such as catheter shaft 102. The diameter of the expandable implant 106 in the collapsed configuration is small enough for the implant to be delivered through the vasculature to the treatment area. In various embodiments, the diameter of the collapsed configuration is small enough to minimize the crossing profile of catheter assembly 100 and reduce or prevent tissue damage to the patient. In the collapsed configuration, the expandable implant 106 can be guided by catheter shaft 102, or another suitable delivery device, through the vasculature.

In various embodiments, expandable implant 106 can comprise a radially expanded configuration suitable for delivering deployment of the implant at the treatment area of a patient's vasculature. In the expanded configuration, the diameter of expandable implant 106 can be approximately the same as the vessel to be repaired. In other embodiments, the diameter of expandable implant 106 in the expanded configuration can be slightly larger than the vessel to be treated to provide a traction fit within the vessel.

In various embodiments, expandable implant 106 can comprise a self-expandable implant, such as a self-expandable stent graft. Such implants dilate from a radially collapsed configuration to a radially expanded configuration when unrestrained. In other embodiments, expandable implant 106 can comprise an implant that is expanded with the assistance of a secondary device such as, for example, a balloon. In yet other embodiments, catheter assembly 100 can comprise a plurality of expandable implants 106. The use of a catheter assembly with any number of expandable implants is within the scope of the present disclosure.

Various expandable implants in accordance with the disclosure comprise a sleeve or multiple sleeves. The sleeve or sleeves can constrain an expandable implant in a collapsed configuration for endoluminal delivery of the implant to a treatment portion of the vasculature of a patient. For the purposes of the disclosure, the term "constrain" can mean (i) to limit the expansion, either through self-expansion or assisted by a device, of the diameter of an expandable implant or (ii) to cover or surround but not otherwise restrain an expandable implant (e.g., for storage or biocompatibility reasons and/or to provide protection to the expandable implant and/or the vasculature). For example, catheter assembly 100 comprises sleeve 104. Sleeve 104 surrounds and constrains expandable implant 106 to a reduced diameter.

After deployment, the sleeve or sleeves can be removed in order to allow the expandable implant to expand to its functional diameter and achieve the desired therapeutic outcome. The sleeve or sleeves can remain implanted while not interfering with the expandable implant.

In various embodiments, an expandable implant is constrained by a single sleeve which circumferentially surrounds the expandable implant. For example, with reference to FIG. 1, catheter assembly 100 comprises a sleeve 104. In various embodiments, sleeve 104 circumferentially surrounds expandable implant 106 and constrains it in a collapsed configuration, in which the diameter is less than the diameter of the unconstrained implant. For example, sleeve 104 can constrain expandable implant 106 in a collapsed configuration for delivery within the vasculature.

In other embodiments, an expandable implant is constrained by a plurality of sleeves which circumferentially surround the expandable implant. The plurality of sleeves can comprise at least two sleeves which circumferentially surround each other.

In various embodiments, sleeves can be tubular and serve to constrain an expandable implant. In such configurations, sleeves are formed from a sheet of one or more materials wrapped or folded about the expandable implant. While the illustrative embodiments herein are described as comprising one or more tubular sleeves, sleeves of any non-tubular shape that corresponds to an underlying expandable implant or that are otherwise appropriately shaped for a given application are also within the scope of the present disclosure.

In various embodiments, sleeves are formed by wrapping or folding the sheet of material(s) such that two parallel edges of the sheet are substantially aligned. Said alignment can or cannot be parallel to or coaxial with the catheter shaft of a catheter assembly. In various embodiments, the edges of the sheet of material(s) do not contact each other.

In various embodiments, the edges of the sheet of material(s) do contact each other and are coupled with a coupling member (as described below), an adhesive, or the like. In various other embodiments, the edges of the sheet of material(s) are aligned so that the edges of the same side of the sheet or sheets (e.g., the front or back of the sheet) are in contact with each other. In still other embodiments, the edges of opposite sides of the sheet of material(s) are in contact with each other, such that the edges overlap each other, such that a portion of one side of the sheet is in contact with a portion of the other side. Said another way, the front of the sheet can overlap the rear of the sheet, or vice versa.

In various embodiments, sleeves comprise materials similar to those used to form a graft member. For example, a precursor flexible sheet used to make the sleeve can be formed from a flattened, thin wall ePTFE tube. The thin wall tube can incorporate "rip-stops" in the form of longitudinal high strength fibers attached or embedded into the sheet or tube wall.

The sheet of material(s) used to form the sleeve(s) can comprise a series of openings, such that the openings extend from one edge of the sheet to the other. In such configurations, a coupling member can be woven or stitched through the series of openings in the sheet of material(s), securing each of the two edges together and forming a tube. For example, in FIG. 1, coupling member 134 secures the edges of sleeve 104 such that sleeve 104 maintains expandable implant 106 in a reduced diameter.

In various embodiments, the coupling member can comprise a woven fiber. In other embodiments, the coupling member can comprise a monofilament fiber. Any type of string, cord, thread, fiber, or wire which is capable of maintaining a sleeve in a tubular shape is within the scope of the present disclosure.

In various embodiments, a single coupling member can be used to constrain the diameter of one or more sleeves. In other embodiments, multiple coupling members can be used to constrain the diameter of one or more sleeves.

In various embodiments, once a suitable expandable implant is in a collapsed configuration, the expandable implant can be deployed within the vasculature of a patient. An expandable implant in a collapsed configuration can be introduced to a vasculature and directed by a catheter assembly to a treatment area of the vasculature. Once in position in the treatment area of the vasculature, the expandable implant can be expanded to an expanded configuration.

In various embodiments, when the expandable implant is in position within the vasculature, the coupling member or members can be disengaged from the sleeve or sleeves from outside of the body of the patient, which allows the sleeve(s) to open and the expandable implant to expand. As discussed above, the expandable implant can be self-expanding, or the implant can be expanded by a secondary device, such as a balloon.

The coupling member or members can be disengaged from the sleeve or sleeves by a mechanical mechanism operated from outside of the body of the patient. For example, the member or members can be disengaged by applying sufficient tension to the member or members. In another example, a dial or rotational element can be attached to the coupling member or members outside of the body. Rotation of the dial or rotational element can provide sufficient tension to, displace and disengage the coupling member or members.

In other configurations, coupling member or members can be disengaged by non-mechanical mechanisms, such as, for example, dissolution, by providing ultrasonic energy. In such configurations, sufficient ultrasonic energy is provided to coupling member or members to disengage them from the sleeve or sleeves.

In various embodiments, disengaging a single coupling member which closes a single sleeve from the sleeve allows the expandable implant to be expanded. For example, with reference to FIG. 1, catheter assembly 100 can be used to deliver an implant expandable implant 106 to a treatment area of a vasculature. Expandable implant 106 has a collapsed diameter for delivery, and sleeve 104 circumferentially surrounds expandable implant 106 and is held closed by coupling member 134. As described in more detail below, bending of expandable implant 106 can be controlled prior to full expansion (e.g., at an intermediate diameter) to help facilitate delivery to the desired position. Once expandable implant 106 is in position relative to the treatment area, coupling member 134 is disengaged from sleeve 104 and sleeve 104 is released, allowing expandable implant 106 to expand to a larger diameter.

As mentioned above, in various embodiments of the present disclosure, an expandable implant can further comprise an intermediate configuration. In the intermediate configuration, the diameter of the expandable implant is constrained in a diameter smaller than the expanded configuration and larger than the collapsed configuration. For example, the diameter of the expandable implant in the intermediate configuration can be about 50% of the diameter of the expandable implant in the expanded configuration.

However, any diameter of the intermediate configuration which is less than the diameter of the expanded configuration and larger than the collapsed configuration is within the scope of the invention.

In such embodiments, the expandable implant can be expanded from the collapsed configuration to the intermediate configuration once the implant has been delivered near the treatment area of the vasculature of a patient. The intermediate configuration can, among other things, assist in properly orienting and locating the expandable implant within the treatment area of the vasculature.

In various embodiments, an expandable implant can be concentrically surrounded by two sleeves having different diameters. In such configurations, a primary sleeve constrains the expandable implant in the collapsed configuration. Once the collapsed configuration sleeve is opened, a secondary sleeve constrains the expandable implant in the intermediate configuration. As discussed above, the expandable implant can be self-expanding, or the implant can be expanded by a secondary device, such as a balloon.

Figure 2:
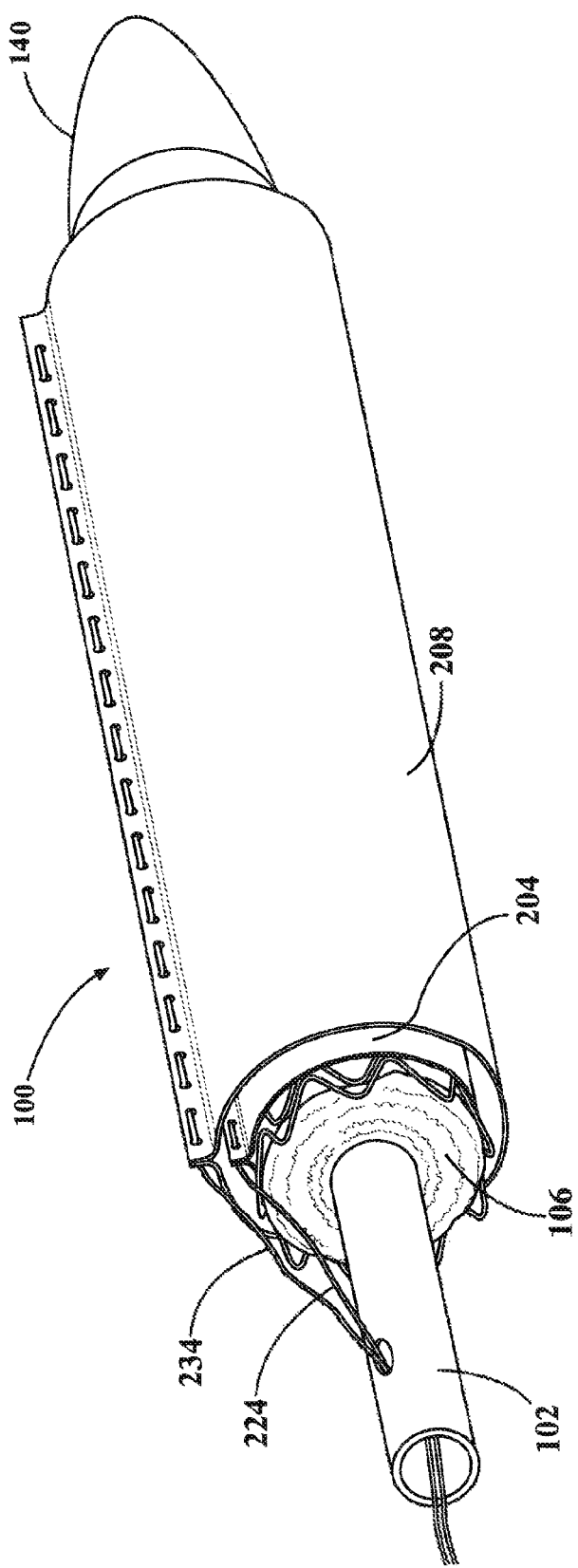
FIG. 2 illustrates a perspective view of a catheter assembly having an expandable implant in accordance with the present disclosure.
Figure 3A:
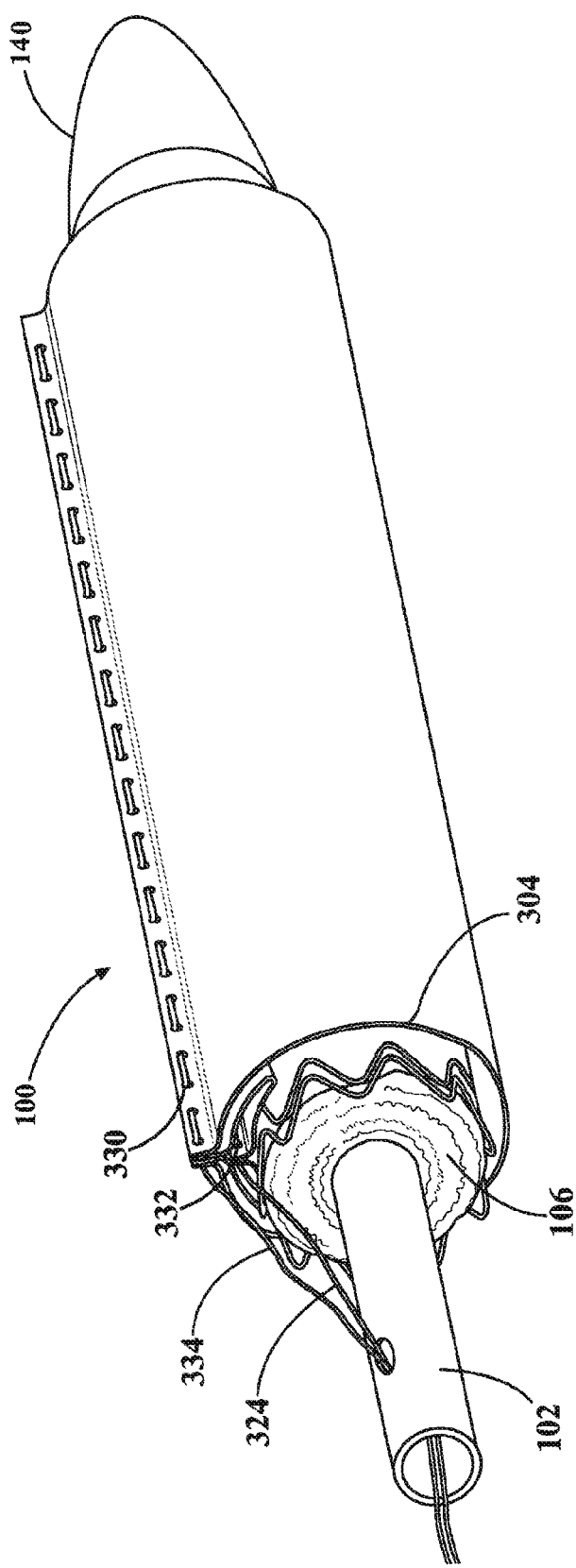
FIGS. 3A-3E illustrate a perspective view, two cross-sectional views, and two other perspective views, respectively, of a catheter assembly having an expandable implant in accordance with the present disclosure.
Figure 3B:
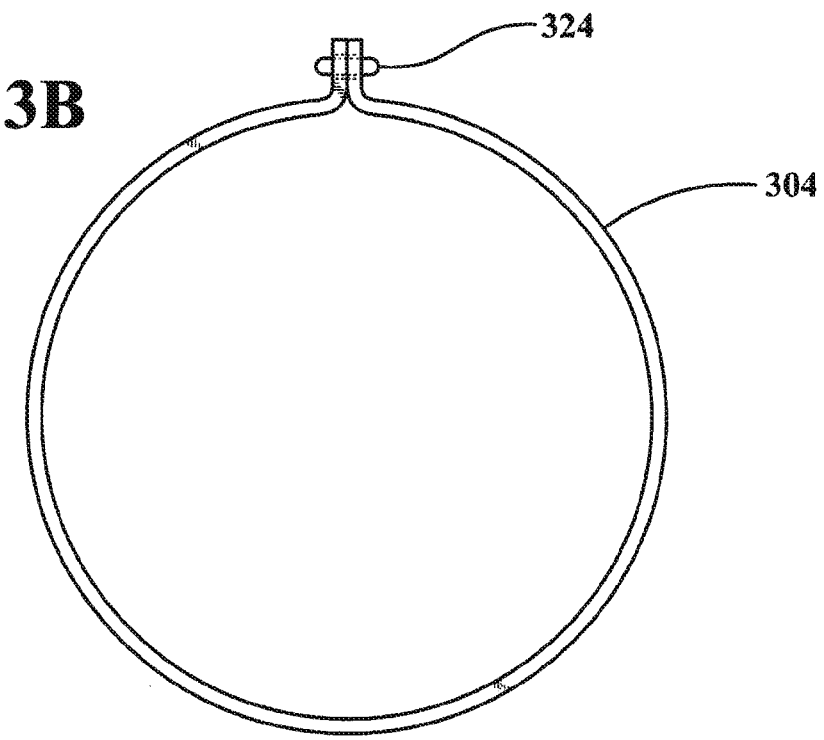
Figure 3C:
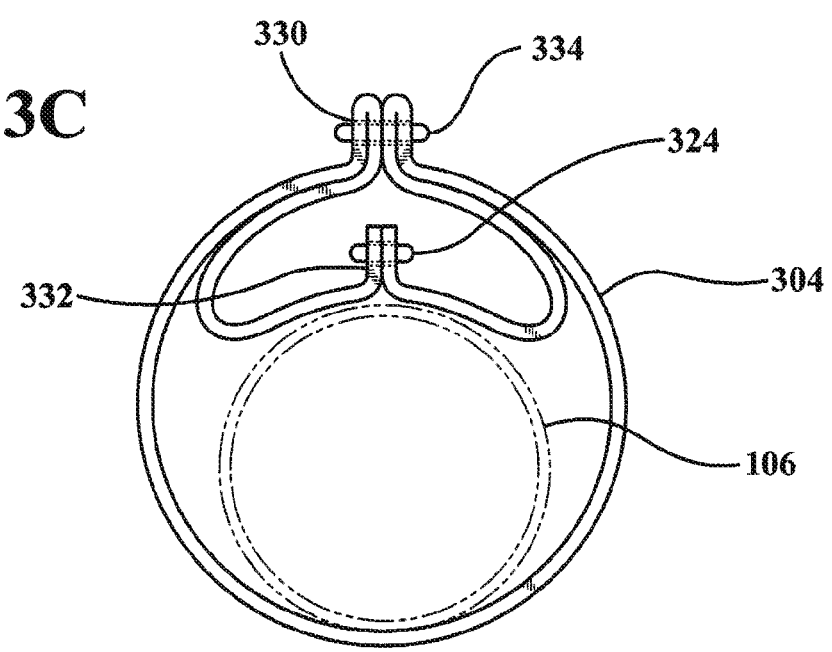
Figure 3D:
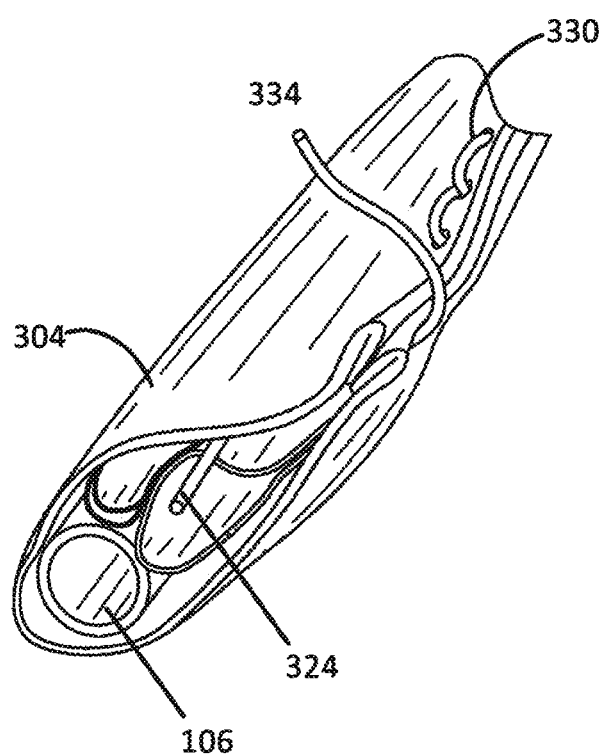
Figure 3E:
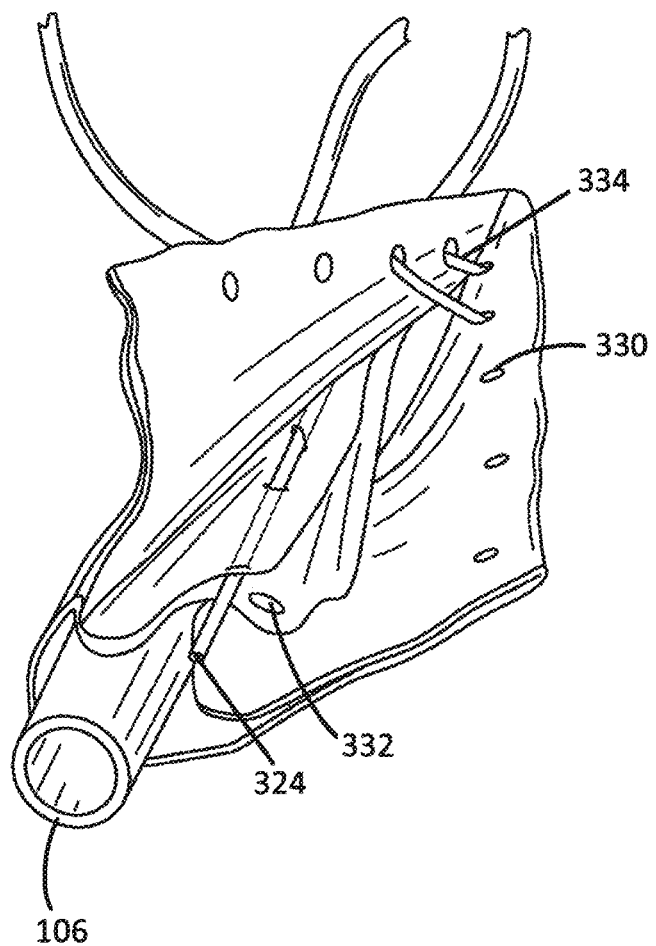

For example, with reference to FIG. 2, a catheter assembly 100 comprises an expandable implant 106 and secondary sleeve 204. Secondary sleeve 204 constrains expandable implant 106 to an intermediate configuration. Secondary sleeve 204 is held in position around expandable implant 106 by secondary coupling member 224.

Catheter assembly 100 further comprises primary sleeve 208, which constrains expandable implant 106 in a collapsed configuration for delivery to the vasculature of a patient. Primary sleeve 208 is held in position around expandable implant 106 by primary coupling member 234.

Once expandable implant 106 is sufficiently close to the treatment area of the vasculature, primary coupling member 234 is disengaged from primary sleeve 208, which releases primary sleeve 208 and allows expanded implant 106 to expand to a larger diameter.

After primary sleeve 208 has been expanded, secondary sleeve 204 constrains the expandable implant 106 in the intermediate configuration. In the intermediate configuration, as mentioned above and as described in more detail below, expandable implant 106 can be oriented and adjusted (e.g., by bending and torsional rotation) to a desired location within the treatment area of the vasculature.

In other embodiments of the present disclosure, a single sleeve can be used to constrain the expandable implant in both a collapsed configuration and an intermediate configuration. For example, with reference to FIGS. 3A-3E, catheter assembly 100 comprises an expandable implant 106, a monosleeve 304, a primary coupling member 334, and a secondary coupling member 324.

Monosleeve 304 further comprises a plurality of secondary holes 332. In this configuration, secondary coupling member 324 is stitched or woven through secondary holes 332, constricting monosleeve 304 and expandable implant 106 to the diameter of an intermediate configuration. In the intermediate configuration, the diameter of expandable implant 106 is less than the expanded diameter and larger than the diameter of the collapsed configuration. In the intermediate configuration, as described in more detail below, expandable implant 106 can be oriented and adjusted (e.g., by bending and torsional rotation) to a desired location within the treatment area of the vasculature.

Monosleeve 304 further comprises a plurality of primary holes 330. In this configuration, primary coupling member 334 is stitched or woven through primary holes 330, constricting monosleeve 304 and expandable implant 106 to the diameter of the collapsed configuration. The diameter of the collapsed configuration is selected to allow for delivery of the expandable implant 106 to the treatment area of the vasculature of a patient.

Once expandable implant 106 has been delivered to a region near the treatment area of the vasculature, primary coupling member 334 can be disengaged from monosleeve 304, allowing expandable implant 106 to be expanded to the intermediate configuration. Expandable implant 106 can be oriented and adjusted (e.g., by bending and torsionally rotating) to a desired location within the treatment area of the vasculature. After final positioning, secondary coupling member 324 can be disengaged from monosleeve 304, and expandable implant 106 can be expanded to the expanded configuration.

Although a number of specific configurations of constraining members (for example, primary and secondary members) and sleeves (for example, primary and secondary sleeves) have been discussed, the use of any number and/or configuration of constraining members and any number of sleeves is within the scope of the present disclosure.

Figure 4A:
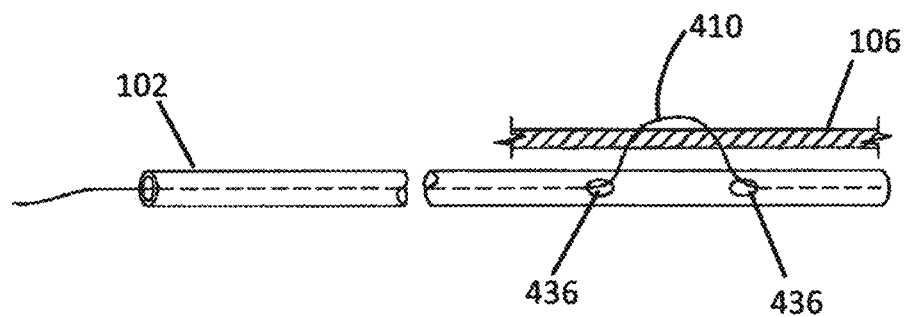
FIGS. 4A and 4B illustrate partial cross-sectional views of a catheter assembly having an expandable implant.
Figure 4B:
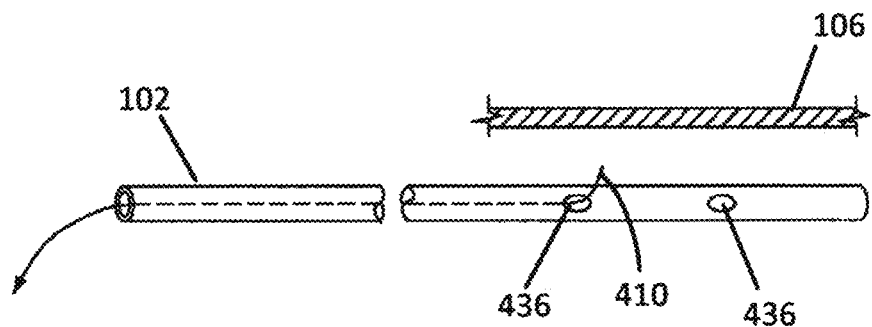
Figure 5:
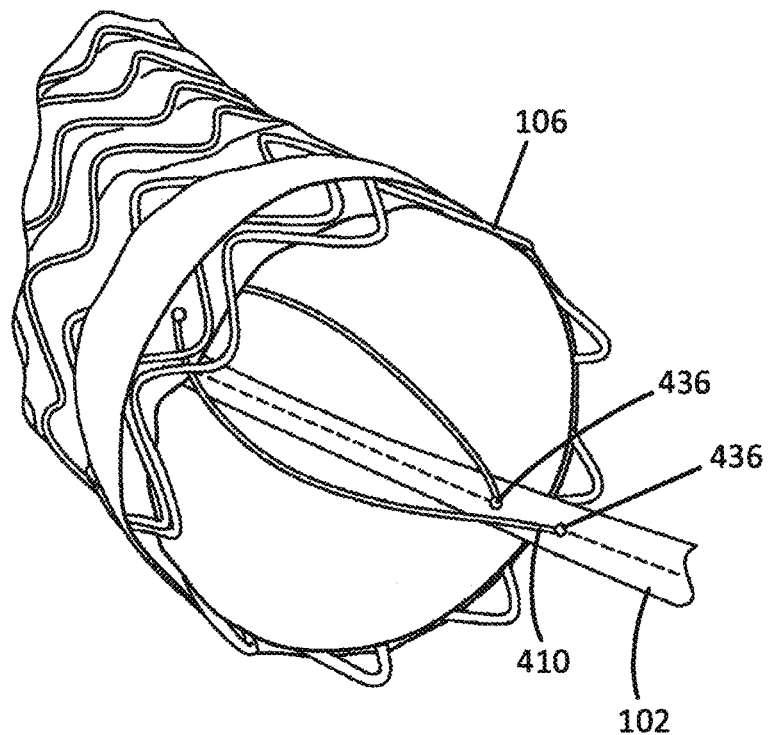
FIG. 5 illustrates a perspective views of a catheter assembly having an expandable implant in accordance with the present disclosure.

In various embodiments, catheter assembly 100 further comprises a lockwire. Such a lockwire can be used to interact with and secure one or more portions of an expandable implant to a catheter shaft to orient and assist in positioning the expandable implant. For example, with initial reference to FIGS. 4A, 4B, and 5, catheter assembly 100 comprising a catheter shaft 102 and a lockwire 410 is illustrated. Catheter shaft 102 can comprise one or more ports 436. In various embodiments, lockwire 410 extends from the trailing end of catheter assembly 100 through catheter shaft 102, exits a port 436, interacts with expandable implant 106, and reenters catheter shaft 102 through a port 436, wherein the exit and reentry port(s) can be the same or different port(s). As illustrated in FIG. 4B, lockwire 410 can be disengaged with expandable implant 106 by applying sufficient tension in the direction of the trailing end of catheter assembly 100, causing lockwire 410 to be withdrawn and/or to break. However, any manner of securing an expandable implant to the catheter shaft to facilitate orientation and positioning of the expandable implant is within the scope of the present disclosure.

In various embodiments, expandable implant 106 can comprise an apposition line which allows a user or operator to control the curvature of expandable implant 106. For example, an apposition line can be configured to facilitate deployment of expandable implant 106 at tortuous treatment sites, such as the aortic arch, where an end of expandable implant 106 might otherwise fail to conform, engage, and form a seal with the surrounding tissue due to straightening out or rotation of the expandable implant.

Figure 6A:
FIGS. 6A-6D illustrate side views of various stages of deployment of a catheter assembly having an expandable implant in accordance with the present disclosure.
Figure 6B:
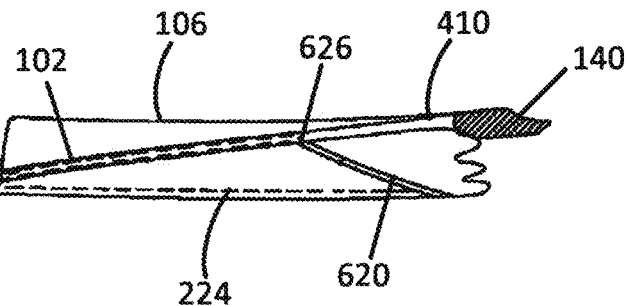

For example, with initial reference to FIG. 6B, a catheter assembly 100 comprising an apposition line 620 is illustrated. In various embodiments, apposition line 620 can interact with catheter shaft 102 and expandable implant 106 to allow for manipulation of the shape of expandable implant 106 by the user or operator of catheter assembly 100. For example, tension can be applied to apposition line 620 to bend expandable implant 106 to a desired shape and/or curvature. Apposition line 620 can, for example, maintain a curvature which generally conforms to the shape of, for example, a tortuous anatomy. Maintaining such a curvature can allow expandable implant 106 to fully engage the surrounding tissue and form a seal.

In various embodiments, apposition line 620 can extend from the trailing end of catheter assembly 100 through catheter shaft 102 to the distal end of expandable implant 106. For example, apposition line 620 can extend from the trailing end of catheter assembly 100 through catheter shaft 102 to a side port 626, where it exits catheter shaft 102 through side port 626 and extends to the distal end of expandable implant 106. In such configurations, apposition line 620 can engage with the distal end of expandable implant 106. While apposition line can terminate at the distal end of expandable implant 106, in various embodiments, apposition line 620 can extend from the distal end of expandable implant 106 back towards side port 626, enter the port, and return toward the trailing end of catheter assembly 100.

Figure 7:
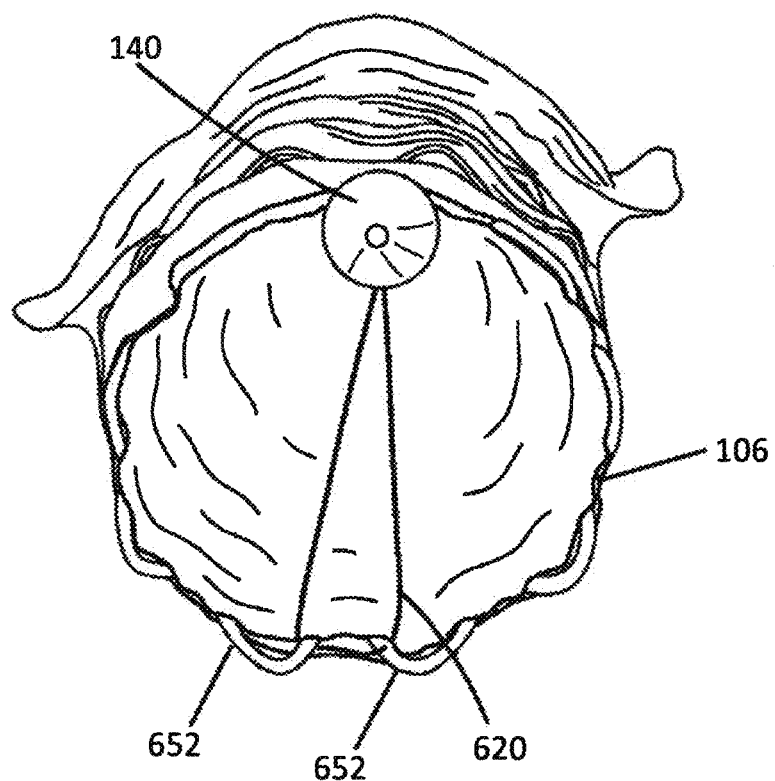
FIG. 7 illustrates a front view of a catheter assembly having an expandable implant in accordance with the present disclosure.

With initial reference to FIG. 7, in embodiments in which expandable implant 106 is a stent, a single apposition line 620 can engage with the distal end of expandable implant 106 by, for example, looping around one or more wire frame apices 652. In embodiments in which expandable implant 106 is a stent graft, apposition line 620 can loop around wire frame apices 652 and/or through the side wall of the graft member of expandable implant 106. However, any manner in which apposition line 620 can be engage with an expandable implant such that the curvature of the implant can be controlled is within the scope of the present disclosure.

In various embodiments, apposition line 620 can comprise can comprise metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol. Elongated members or lock wires can also be formed from high strength polymer fibers such as ultra high molecular weight polyethylene fibers (e.g., Spectra®, Dyneema Purity®, etc.) or aramid fibers (e.g., Technora®, etc.). However, any material capable of providing sufficient tension to and maintaining the curvature of an expandable implant is within the scope of the present disclosure.

With reference to FIGS. 6A-6D, cross-sectional views of various expandable implant configurations are illustrated. FIGS. 6A-6D generally illustrate a deployment sequence of catheter assembly 100 utilizing apposition line 620 to maintain a curvature of expandable implant 106 as the implant deployed along a curved or tortuous anatomy, such as, for example, the aortic arch.

As illustrated in FIG. 6A, expandable implant 106 comprises a stent graft. Expandable implant 106 is constrained in the collapsed configuration by, for example, a flexible constraining sleeve, and deployed endoluminally toward a treatment site in the body of a patient.

FIG. 6B illustrates expandable implant 106 in an intermediate configuration. In such embodiments, catheter shaft 102 can comprise a side port 626. Side port 626 can be located at a position on catheter shaft 102 between the proximal and distal ends of expandable implant 106.

Figure 6C:
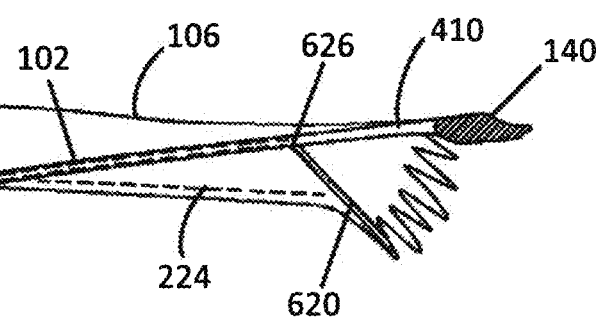
Figure 6D:
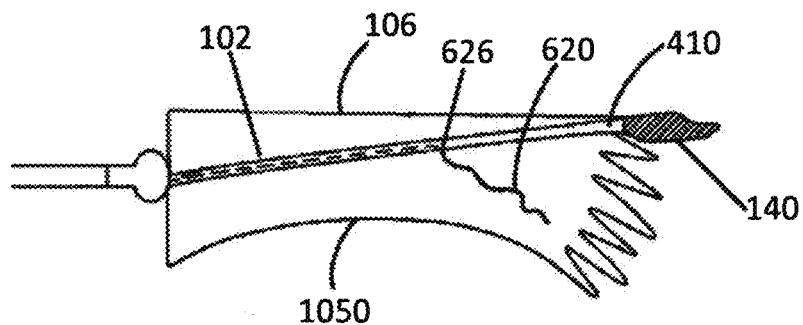

In various embodiments, expandable implant 106 can be secured to catheter shaft 102 near the proximal and/or distal ends of expandable implant 106. For example, as illustrated in FIGS. 6B-6D, expandable implant 106 is secured to catheter shaft 102 by lockwire 410 at both the proximal and distal ends of expandable implant 106. In the illustrated embodiment, the portion of expandable implant 106 secured at the distal end is approximately 180 degrees out of phase with the portion of expandable implant 106 secured at the proximal end. This configuration offsets catheter shaft 102 in relation to expandable implant 106. Stated another way, in such configurations, catheter shaft 102 is not parallel to a longitudinal axis of expandable implant 106. However, any relative orientation of catheter shaft 102 and expandable implant 106 which permits the proper orientation and positioning of expandable implant 106 is within the scope of the present disclosure.

As illustrated in FIGS. 6B-6D, catheter assembly 100 can comprise an apposition line 620. In such embodiments, apposition line 620 extends from the trailing end of catheter assembly 100 through catheter shaft 102 and exits side port 626. Apposition line 620 further extends to the distal end of and engages expandable implant 106, then returns to catheter shaft 102 through side port 626.

In various embodiments, with initial reference to FIG. 6C, further deployment of expandable implant 106 can be initiated by partially releasing secondary coupling member 224. For example, as secondary coupling member 224 is partially released, the distal end of expandable implant 106 can begin to expand to the expanded configuration. In such embodiments, as the distal end expands, tension applied to apposition line 620 causes the distal end to curve in a desired direction. For example, as illustrated in FIG. 6C, the distal end of expandable implant 106 can curve away from catheter tip 140.

As illustrated in FIGS. 6C and 6D, as secondary coupling member 224 is released from expandable implant 106, tension applied to apposition line 620 can cause expandable implant 106 to conform to a desired curvature 1050. In various embodiments, the shape of curvature 1050 is dependent on a number of factors, such as, for example, the position of side port 626 along catheter shaft 102 and the resilience of expandable implant 106, among others. Curvature 1050 can be chosen to correspond with the shape and/or profile of a portion of the treatment area, such as, for example, a vessel. Once a suitable curvature 1050 is selected, the attributes of catheter assembly 100 can be selected to provide curvature 1050.

In various embodiments, catheter assembly 100 further comprises an end-constraining element. For example, an end-constraining element can assist in controlling the outer peripheral dimension of an end of expandable implant 106 to facilitate repositioning of the implant during deployment at the treatment site. For example, with initial reference to FIG. 8, catheter assembly 100 comprises an end-constraining constraining element 612. In such configurations, end-constraining element 612 can assist in maintaining expandable implant 106 in a compressed and/or intermediate configuration.

Figure 8:
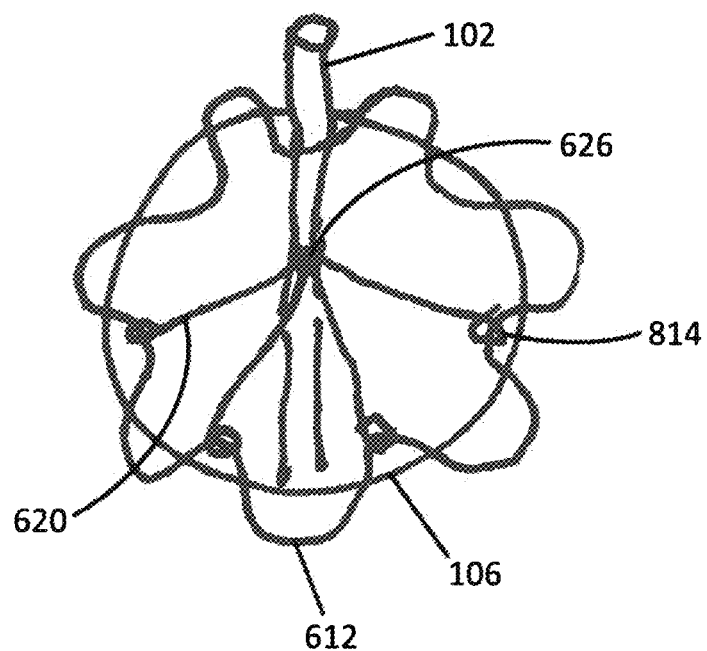
FIG. 8 illustrates a front view of a catheter assembly having an expandable implant in accordance with the present disclosure.

As illustrated in FIG. 8, end-constraining element 612 can be configured to concentrically surround the distal end of expandable implant 106. In various embodiments, end-constraining element 612 comprises a thread or fiber that extends from the trailing end of catheter assembly 100, through catheter shaft 102, and to the distal end of expandable implant 106. During deployment of expandable implant 106, tension can be applied to end-constraining element 612 to maintain the distal end in a collapsed and/or intermediate configuration. By selectively releasing the tension applied to end-constraining element 612, the rate of expansion of the distal end of expandable implant 106 which can, for example, assist in conforming expandable implant 106 to a desired curvature.

For example, end-constraining element 612 can be controlled such that movement of a dial or other control mechanism in a first direction relative to catheter shaft 102 shortens the portion of the element that extends around expandable implant 106, radially compressing the implant. Movement of a dial or control mechanism in an opposite second direction relative to catheter shaft 102 lengthens the portion of element that extends around expandable implant 106, allowing radial expansion of the implant. Thus, selective displacement of the movable element between the first and second directions results in compression and expansion, respectively, of expandable implant 106 to facilitate positioning of the implant during deployment at the treatment site.

Figure 9:
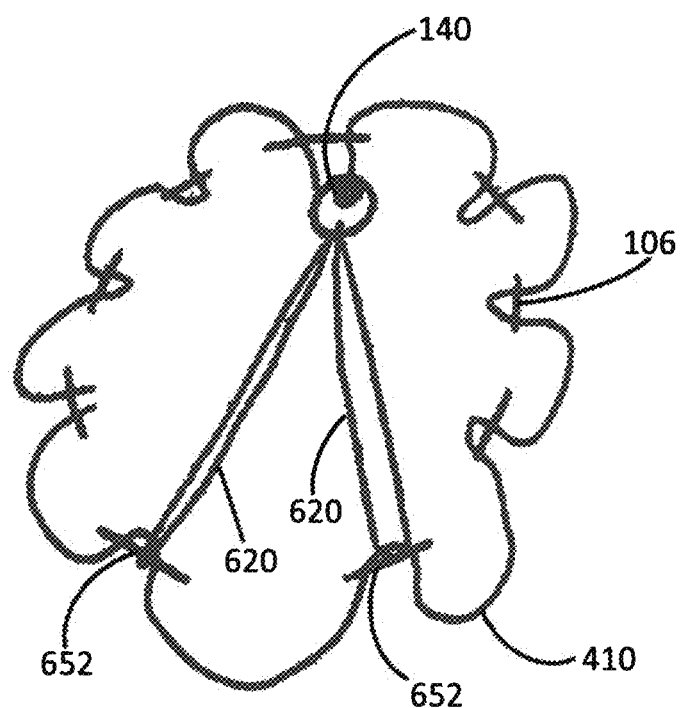
FIG. 9 illustrates a front view of a catheter assembly having an expandable implant in accordance with the present disclosure.

In various embodiments, catheter assembly 100 further comprises two or more apposition lines 620. Multiple apposition lines can assist, for example, in conforming expandable implant 106 to a desired curvature. For example, with initial reference to FIG. 9, catheter assembly 100 can comprise two apposition lines 620. In such configurations, each apposition line 620 can engage with apices 652 of expandable implant 106.

With returned reference to FIG. 8, catheter assembly 100 can further comprise one or more eyelets 814. In various embodiments, eyelets 814 can be located at the end of each apposition line 620 nearest the distal end of expandable implant 106. As illustrated in FIG. 8, catheter assembly 100 can comprise multiple apposition lines 620, each comprising an eyelet 814. In such embodiments, end-constraining element 612 can be configured such that the element passes through both the distal end of expandable implant 106 and one or more eyelets 814 of apposition lines 620.

Figure 10:
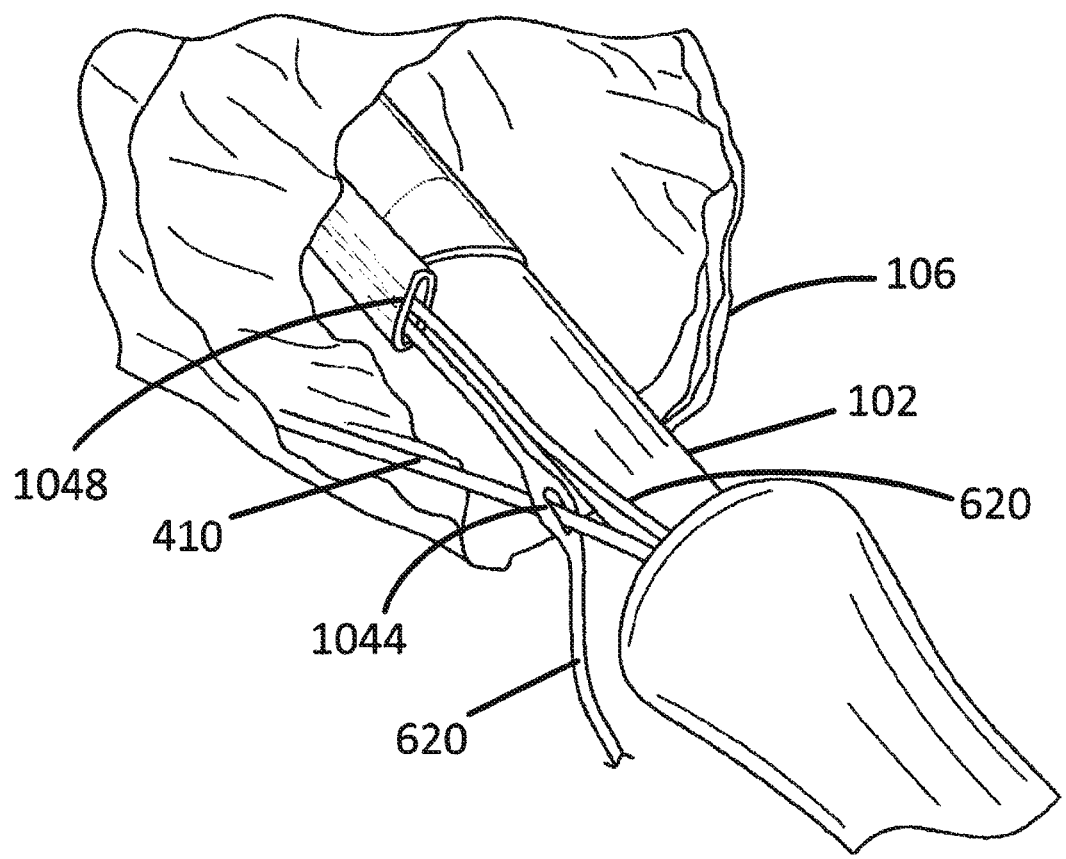
FIG. 10 illustrates a perspective view of a catheter assembly having an expandable implant in accordance with the present disclosure.

In various embodiments, as illustrated in FIG. 10, catheter assembly 100 comprises a shrink tube 1048. For example, apposition line 620 can extend through shrink tube 1048 towards the distal end of expandable implant 106, engage with a portion of the implant, and return through shrink tube 1048 to the proximal end of the implant. In such configurations, apposition line 620 can comprise an eyelet 1044. Eyelet can, for example, engage with end-constraining element. Such engagement can help maintain the relative positions of apposition line and end-constraining element.

In various embodiments, catheter assembly 100 can comprise one or more apposition lines 620. For example, apposition lines 620 can extend through shrink tube 1048 to the distal end of expandable element 106. In such configurations, apposition lines 620 can be simultaneously actuated relative to catheter shaft 102. Alternatively, each apposition line 620 can be configured for separate actuation to provide additional control curvature of expandable implant 106.

After a sufficient degree of bending has been achieved in expandable implant 106, such as, for example, by achieving a desired curvature, the expandable implant 106 can be rotated for final positioning in the treatment area of the vasculature. In various exemplary embodiments, lockwire 410 is engaged with apposition line 620 such that torsional rotation of the catheter shaft causes expandable implant 106 to rotate within the vasculature. However, any configuration of catheter assembly 100 which allows for rotation of expandable implant 106 is within the scope of the present disclosure.

In various embodiments, an expandable implant can further comprise one or more radiopaque markers. In one embodiment, one or more radiopaque markers form a band around the distal end of the expandable implant. In such configurations, the radiopaque markers can assist in deployment of an expandable implant by providing increased visibility when observing the expandable implant with a radiographic device, such as an x-ray machine. Any arrangement of radiopaque markers which assists in deployment of an expandable implant is within the scope of the present disclosure.

Figure 11:
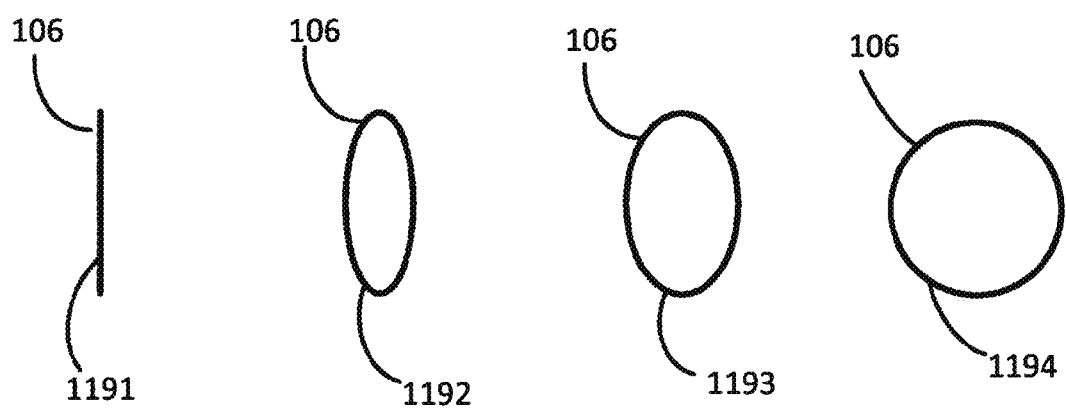
FIG. 11 illustrates various profile views of a distal end of an expandable implant.

For example, radiopaque markers can assist in orienting the expandable implant by providing a profile view of the distal end of the expandable implant. For example, with reference to FIG. 11, a number of potential profiles 1191-1194 of the distal end of an expandable implant 106 are illustrated. In such configurations, radiopaque markers located in the distal end of expandable implant 106 provide a profile view of the distal end of expandable implant 106 when viewed by a radiographic device. Such profile views can be used to properly orient expandable implant 106 by assisting a user in determining the degree of rotation and/or orientation of a bend in expandable implant 106.

For example, profile 1191 represents a distal end of an expandable implant 106 having an orientation substantially orthogonal to a radiographic image capture device, such as an x-ray camera. Profile 1192 represents a distal end of an expandable implant having an orientation less orthogonal than profile 1191. Profile 1193 represents a distal end of an expandable implant 106 having an orientation less orthogonal than profile 1192. Finally, profile 1194 represents a distal end of an expandable implant 106 having an orientation parallel to a radiographic image capture device.

After expandable implant 106 has been properly oriented and located within the treatment area of the patient, secondary coupling member 224 can be disengaged from secondary sleeve 204. Once secondary coupling member 224 is disengaged from secondary sleeve 204, expandable implant 106 can be expanded to a final position and diameter within the treatment area. In various exemplary embodiments, secondary sleeve 204 is removed from the vasculature. In other exemplary embodiments, secondary sleeve 204 remains in position circumferentially surrounding a portion of expandable implant 106.

Upon full deployment of expandable implant 106, catheter shaft 102 can be disengaged from expandable implant 106 to allow catheter assembly 100 to be removed from the body of the patient. In various embodiments, catheter shaft 102 is disengaged from expandable implant 106 by removing lockwire 410. In various embodiments, as illustrated in FIGS. 6A-6D, catheter shaft 102 is engaged by lockwire 410 to portions of the distal and proximal ends of expandable implant 106. In such embodiments, tension is applied to lockwire 410, causing it to break and/or disengaged from both ends of expandable implant 106, disengaging catheter shaft 102 from the implant.

In various embodiments, apposition line 620 can be disengaged from the distal end of expandable implant 106. For example, sufficient tension can be applied to apposition line 620 to break apposition line 620. In other configurations, for example shown in FIG. 10, apposition wire 620 is released when lockwire 410 is disengaged and/or broken.

In other embodiments, one or more apposition lines 620 are engaged with end-constraining element 612. In such configurations, for example as shown in FIG. 8, end-constraining element 612 can be disengaged from eyelets 814 of apposition lines 620, allowing for removal of both end-constraining element 612 and the one or more apposition lines 620.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A catheter assembly comprising:
a catheter having a leading end and a trailing end and comprising a main lumen extending between the leading end and the trailing end and a side port;
an expandable implant having a proximal end and a distal end and positioned between the leading end and trailing end of the catheter, the expandable implant having a collapsed configuration for endoluminal delivery of the expandable implant to a treatment site and an expanded configuration having a diameter larger than the diameter of the collapsed configuration,
wherein the side port is located along the main lumen of the catheter at a position between the proximal end and the distal end of the expandable implant;
a primary sleeve wrapped circumferentially around the expandable implant, wherein the primary sleeve comprises a sheet of material having first and second major surfaces and a plurality of openings extending from the first major surface to the second major surface; and
a primary coupling member cooperating with the plurality of openings of the sheet for releasably coupling portions of the sheet to one another to constrain the expandable implant in the collapsed configuration;
a lockwire arranged through the expandable implant adjacent at least one of the proximal end and the distal end thereof, the lockwire being configured to releasably couple the expandable implant to the catheter; and
at least one apposition line including an eyelet through which the lock wire is arranged and being configured to maintain a longitudinal curvature of the expandable implant during expansion of the expandable implant and release when the lockwire is disengaged from the catheter, the at least one apposition line being arranged to extend through the main lumen of the catheter and through the side port of the catheter to engage at least a portion of the expandable implant through a wall of the expandable implant near the distal end and return to the main lumen of the catheter through the side port during engagement of the at least one apposition line with the expandable implant.

2. The catheter assembly of claim 1, further comprising a secondary sleeve and secondary coupling member, wherein the secondary sleeve limits expansion of the expandable implant to an intermediate configuration having a diameter larger than the diameter of the collapsed configuration and smaller than the diameter of the expanded configuration, and wherein the apposition line is configured to release from the portion of the expandable implant upon disengaging of the lockwire.

3. The catheter assembly of claim 1, wherein the expandable implant comprises a stent graft.

4. The catheter assembly of claim 1, further comprising a secondary coupling member and a plurality of secondary openings, wherein the secondary coupling member cooperates with the plurality of secondary openings for releasably coupling portions of the sheet to one another to constrain the expandable implant in an intermediate configuration, the intermediate configuration having a diameter larger than the collapsed configuration and smaller than the expanded configuration.

5. The catheter assembly of claim 1, further comprising a plurality of apposition lines.

6. The catheter assembly of claim 1, wherein the expandable implant is bendable more than about 90 degrees relative to an axis of the catheter.

7. The catheter assembly of claim 1, wherein the expandable implant is releasably coupled to the catheter.

8. The catheter assembly of claim 7, wherein the catheter further comprises a pair of distal end ports and the lockwire exits the main lumen through one of the pair of distal end ports, engages the expandable implant, and enters the main lumen through the other of the pair of distal end ports to removably couple the catheter and the distal end of the expandable implant.

9. The catheter assembly of claim 1, wherein the expandable implant substantially maintains a desired curvature while the expandable implant is deployed to the expanded configuration.

10. The catheter assembly of claim 1, further comprising a radiopaque marker located at the proximal end of the expandable implant.

11. The catheter assembly of claim 10, wherein the radiopaque marker comprises a band extending around a perimeter of the expandable implant.

12. A method for deploying an expandable implant comprising:
providing a catheter assembly of claim 1;
introducing the leading end of the catheter assembly into a body of a patient;
navigating the leading end of the catheter assembly to the proximity of a treatment area;
partially expanding the expandable implant;
applying tension to the at least one apposition line to achieve a desired curvature in the expandable implant;
fully expanding the expandable implant; and
disengaging the at least one apposition line from the expandable implant.

13. The method of claim 12, wherein the catheter assembly further comprises a secondary coupling member and a plurality of secondary openings, wherein the secondary coupling member cooperates with the plurality of secondary openings for releasably coupling portions of the sheet to one another to constrain the expandable implant in an intermediate configuration, the intermediate configuration having a diameter larger than the collapsed configuration and smaller than the expanded configuration.

14. The method of claim 13, wherein the step of fully expanding the expandable implant comprises disengaging the primary coupling member to expand the expandable implant to the expanded configuration.

15. The method of claim 12, wherein the catheter assembly further comprises a secondary sleeve and secondary coupling member, wherein the secondary sleeve limits expansion of the expandable implant to an intermediate configuration having a diameter larger than the diameter of the collapsed configuration and smaller than the diameter of the expanded configuration.

16. The method of claim 12, wherein the catheter assembly further comprises a plurality of apposition lines.

17. The method of claim 12, wherein the catheter further comprises a pair of distal end ports and the lockwire exits the main lumen through one of the pair of distal end ports, engages the expandable implant, and enters the main lumen through the other of the pair of distal end ports to removably couple the catheter and the distal end of the expandable implant.

18. The method of claim 12, wherein the expandable implant is a self-expanding stent graft.

19. The method of claim 12, wherein the catheter assembly further comprises an end-constraining element located at the proximal end of the expandable implant and configured to maintain the proximal end of the expandable implant in the collapsed configuration.

20. The method of claim 19, wherein the catheter assembly further comprises a lockwire configured to couple a portion of the end-constraining element and the catheter.

* * * * *